United States Patent [19]

Kumagai et al.

[11] Patent Number: 4,925,836

[45] Date of Patent: * May 15, 1990

[54] ANTIBACTERIALLY EFFECTIVE METHODS AND COMPOSITIONS BASED UPON (1R,5S,6S)-2-[(6,7-DIHYDRO-5H-PYRAZOLO[1,2-A][1,2,4]TRIAZOLIUM-6-YL)]THIO-6-[R-1-HYDROXYETHYL]-1-METHYL-CARBAPENEM-3-CAROXYLATE AND SALTS THEREFORE

[75] Inventors: Toshio Kumagai; Hiroshi Matsunaga; Yoshisuke Machida; Yunosuke Nagase; Muneo Hikida; Yoshimitsu Nagao, all of Shiki, Japan

[73] Assignee: Lederle (Japan), Ltd., Tokyo, Japan

[*] Notice: The portion of the term of this patent subsequent to Sep. 12, 2006 has been disclaimed.

[21] Appl. No.: 357,349

[22] Filed: May 26, 1989

Related U.S. Application Data

[63] Continuation of Ser. No. 130,121, Dec. 8, 1987, Pat. No. 4,866,171.

[30] Foreign Application Priority Data

Apr. 11, 1987 [JP] Japan .................. 62-89016

[51] Int. Cl.$^5$ .................. C07D 487/04; A61K 31/40
[52] U.S. Cl. .................. 514/210; 540/350
[58] Field of Search .................. 540/350; 514/210

[56] References Cited

U.S. PATENT DOCUMENTS 4,644,061 2/1987 Kim .................. 540/350

FOREIGN PATENT DOCUMENTS 8514 3/1980 European Pat. Off. .
165384 12/1985 European Pat. Off. .
168707 1/1986 European Pat. Off. .
170073 2/1986 European Pat. Off. .

*Primary Examiner*—Nicholas S. Rizzo
*Attorney, Agent, or Firm*—Wegner & Bretschneider

[57] ABSTRACT

Methods and compositions are provided for controlling or preventing a bacterial infection which are based upon (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate or a pharmaceutically acceptable salt thereof.

2 Claims, No Drawings

ANTIBACTERIALLY EFFECTIVE METHODS AND COMPOSITIONS BASED UPON (1R,5S,6S)-2-[(6,7-DIHYDRO-5H-PYRAZOLO[1,2-A][1,2,4]TRIAZOLIUM-6-YL)]THIO-6-[R-1-HYDROXYETHYL]-1-METHYL-CARBAPENEM-3-CAROXYLATE AND SALTS THEREFORE

This application is a continuation of Ser. No. 130,121, filed Dec. 8, 1987, now U.S. Pat. No. 4,866,171, printed with a grant date of Sept. 12, 1989.

INFORMATION DISCLOSURE STATEMENT

Prior art cited under 37 CFR §1.97:

|    |           | U.S. Patent Documents |                                         |
|----|-----------|-----------------------|-----------------------------------------|
| AA | 4,644,061 | 2-1987                | Kim                                     |
|    |           | Foreign Patent Documents |                                      |
| AB | 168,707   | 1-1986                | European Patent Application (I) (Merck) |
| AC | 170,073   | 2-1986                | European Patent Application (II) (Merck)|
| AD | 165,384   | 12-1985               | European Patent Application (III) Sankyo|
| AE | 8,514     | 3-1980                | European Patent Application (IV) Beecham|

European Application (I) (AB) discloses a broad group of compounds, but never specifically any compound with a structure that is suggestive of the group 5H-pyrazolo[1,2-a]triazolinium-6-yl. Pyridinium compounds are a focal point of the exemplified disclosure, including (5S,6S)-2-[2-(2,3-cyclohexeno-1-pyridinium-)ethylthio]-6-[(R)-1-hydroxyethyl]-1-methyl-carbapenem-3-carboxylate (page 63, lines 1-3). European Application (I) (AB) also includes a disclosure of a list of 97 ring groups at Example 35 (pages 139-145), which discloses 97 heterocyclic rings, including the ring forming the group (5H-pyrazolo[1,2-a]triazolinium-6-yl) (page 140, line 10, left hand entry); if that variable is plugged into the formula at page 139, line 10, this would create the (1R,5S,6S)-2-[(5H-pyrazolo[1,2-a]triazolinium-6-yl)]thio-6-[(R)-1-hydroxyethyl]-1-methyl-carbapenem-3-carboxylate. In order to make the compound most relevant to the instant invention according to the generic teaching of the published patent application, it would be necessary to use a starting material 6-mercapto-5H-pyrazolo[1,2-a]triazolinium halide. However, a method for making 6-mercapto-5H-pyrazolo[1,2-a]triazolinium halide is not described in that application, nor is a method for making it described in the literature. The 2-(2,3-cyclohexeno-1-pyridinium-)ethylthio group which is remote, as it is based upon the pyridinium group which is not suggestive of the instant (5H-pyrazolo[1,2-a]triazolinium-6-yl) group.

Kim (AA) and European Application II (AC) are cumulative. European Patent Application Merck (II) ("AC"), European Patent Application (III) to Sankyo ("AD") and European Patent Application (IV) Beecham ("AE") are cited in the European Search Report for the counterpart European application; each is given the designation "technological background".

SUMMARY OF THE INVENTION

In accordance with a first aspect of the invention there is provided a method of treatment for controlling or preventing a bacterial infection in a subject which comprises administering to said subject an antibacterially effective amount of (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate or a pharmaceutically acceptable salt thereof.

In accordance with a second aspect of the invention there is provided an antibacterial composition comprising an antibacterially effective amount of (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate or a pharmaceutically acceptable salt thereof, and a pharmaceutically acceptable carrier therefor a second aspect of the invention there is provided (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate. This compound also may be in the form of the corresponding acid or pharmaceutically acceptable salt, in which case there is included an anionic group balancing the traizolinium positive charge. As such an anionic group may be mentioned, for example, the chloride, acatate or carbonate. As the salt may be mentioned the alkali metal salts, for example, sodium.

There is provided a method for the preparation of (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate, which comprises contacting (1R,5S,6S)-2-[4-pyrazolidinyl]thio-6-[R-1-hydroxyethyl]-1-methyl-carbapenem-3-carboxylic acid with ethyl formimidate hydrohalide under conditions to introduce iminomethyl substitution at each of the free hydrogen positions of the nitrogen atoms of the pyrazolidinyl nucleus, which would be expected to yield the compound (1R,5S,6S)-6-[(R)-1-hydroxyethyl]-1-methyl-2-[(1,2-diiminomethyl)-4-pyrazolidinyl]-thio-carbapenem-3-carboxylic acid, and recovering the in situ formed (1R,5S,6S)-2-[(6,7-dihydro-5H-pyrazolo]1,2-a][1,2,4]triazolium-6-yl)]thio-6-[R-1-hydroxyethyl]-1-methyl-carbapenem-3-carboxylate. Surprisingly, the (1R,5S,6S)-6-[(R)-1-hydroxyethyl]-1-methyl-2-[(1,2-diiminomethyl)-4-pyrazolidinyl]-thio-carbapenem-3-carboxylic acid is not recovered. The compound is produced in a transitory state, and is converted in situ into the (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate. In a preferred embodiment of this aspect of the invention, the ethyl formimidate hydrohalide is the hydrochloride or hydrobromide, and still more preferably is the hydrochloride. Preferably, the reaction is conducted in the presence of a buffer, which in one embodiment is a phosphate. The pH is generally from about 5 to about 9, and more preferably 6 to about 7.5, and the temperature is generally from about −15° C. to about 30° C., and preferably from about −5° C. to about +10° C.

DETAILED DESCRIPTION

As used herein, and unless otherwise specified, the compound "I" refers to both the compound (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3- carboxylate, as well as the acid or pharmaceutically acceptable salt of such compound which includes an anionic group balancing the traizolinium positive charge. The compound (I) manifest high antibacterial activity, a strong action of inhibiting β-lactamase as well as improved resistance to kidney dehydropeptidase. The carbapenem compound (I) may be prepared by reacting a compound identified as the compound (II):

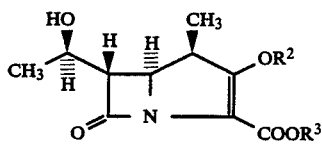

wherein $R^3$ is a carboxyl protecting group, and $R^a$ is an acyl group.
with a mercapto reagent represented by the formula (III):

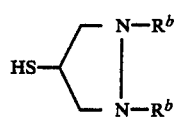

wherein $R^b$ is an amino protecting group.
to give a compound represented by the formula (IV):

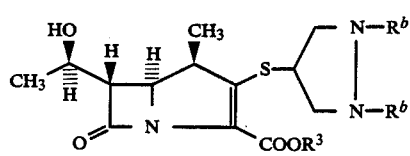

wherein $R^3$ and $R^b$ have the same meanings as above. and subjecting the compound of the formula (IV) to removal of the protecting groups $R^3$ and $R^b$ to give the carbapenem compound of the formula (V).

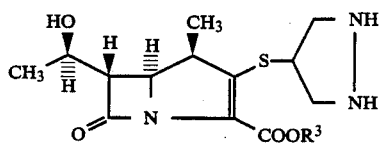

and then, reacting the resulting compound of the formula (V) with alkyl formimidate to give the carbapenem compound represented by the above formula (I).

Immediately after the reaction of the compound (V) with the alkyl formimidate, a compound (1R,5S,6S)-6-[(R)-1-hydroxyethyl]-1-methyl-2-[(1,2-diiminomethyl)-4-pyrazolidinyl]-thio-carbapenem-3-carboxylic acid is formed, which exists briefly before there is conversion to the final product (I). Under the conditions of the present synthesis, the intermediate compound (1R,5S,6S)-6-[(R)-1-hydroxyethyl]-1-methyl-2-[(1,2-diiminomethyl)-4-pyrazolidinyl]-thio-carbapenem-3-carboxylic acid is not recovered but exists only as a transitory intermediate.

The carbapenem compound represented by the formula (II) to be employed as a starting compound in the process described above is known per se and may be prepared in such a manner as disclosed, for example, in Japanese Patent Publication (Laid-Open) No. 123,985/1981 or, more preferably, in accordance with the spatially selective method as indicated in Reaction Scheme A below and proposed by the present inventors (as disclosed, for example, in Japanese Patent Application No. 315,444/1986).

REACTION SCHEME A

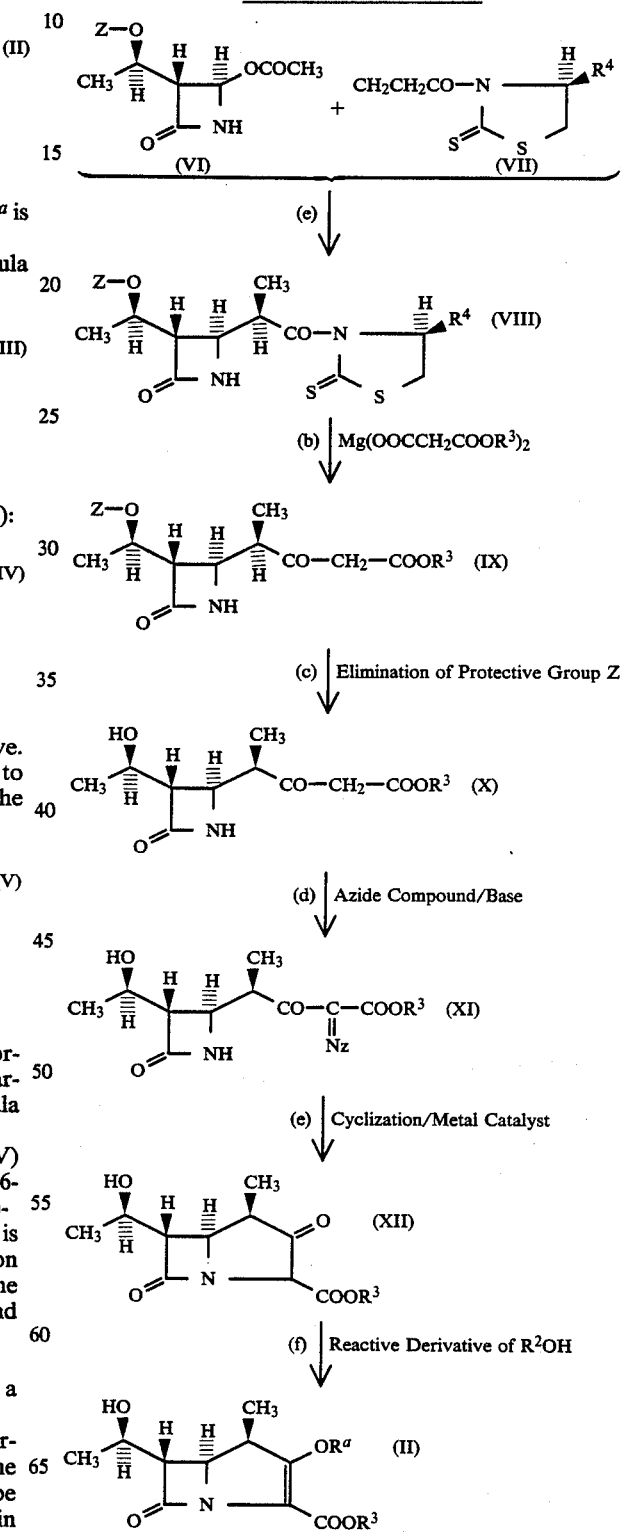

wherein $R^4$ is hydrogen atom or a lower alkyl group; Z is tertiary-butyldimethylsilyl group; and $R^3$ and $R^a$ have the same meanings as above.

In the specification of the present application, the term "lower" stands for a group or a compound affixed with this term as having the numer of carbon atoms ranging from 1 to 7, preferably from 1 to 4.

The term "lower alkyl" referred to herein stands for a straight-chained or branched-chain hydrocarbon group having preferably from 1 to 6 carbon atoms and may include, for example, methyl, ethyl, n-propyl, isopropyl, n-butyl, isobutyl, sec-butyl, tert.-butyl, n-pentyl, isopentyl, n-hexyl, isohexyl or the like.

The term "carboxyl protecting group" referred to herein stands for any group capable of protecting the carboxyl group of the compound involved without adversely affecting any other substituents and the reactions that follow and may include, for example, an ester residue such as a lower alkyl ester residue including, for example, methyl ester, ethyl ester, n-propyl ester, isopropyl ester, n-, iso-, sec- or tert.-butyl ester, n-hexyl ester or the like; an aralkyl ester residue including, for example, benzyl ester, p-nitrobenzyl ester, o-nitrobenzyl ester, p-methoxybenzyl ester or the like; and a lower aliphatic acyloxymethyl ester residue including, for example, acetoxymethyl ester, propionyloxymethyl ester, n- or iso-butyryloxymethyl ester, pivaloyloxymethyl ester or the like.

The term "acyl group" referred to herein stands for, in a narrower sense, a moiety obtainable by removing the hydroxyl group from the carboxyl group of an organic carboxylic acid as well as, in a broader sense, any acyl group derived from an organic sulfonic acid or an organic phosphoric acid. Such an acyl group may include, for example, a lower alkanoyl group such as acetyl, propionyl, butyryl or the like; a (halo)lower alkyl sulfonyl group such as methanesulfonyl, trifluoromethanesulfonyl or the like; a substituted or unsubstituted arylsulfonyl group such as benzenesulfonyl, p-nitrobenzenesulfonyl, p-bromobenzenesulfonyl, toluenesulfonyl, 2,4,6-triisopropylbenzenesulfonyl or the like; and diphenylphosphoryl.

The term "amino protecting group" referred to herein stands for groups usually employed in peptide chemistry, for example, phthaloyl, benzyloxycarbonyl, tert-butoxycarbonyl, p-nitrobenzyloxycarbonyl or the like.

Each of the steps of the Reaction Scheme A above for preparing the compounds represented by the formula (II) in a highly spatial selectivity will be described below more in detail.

The step (a) involves the reaction of the N-propionyl-1,3-thiazoline-2-thione derivative of the formula (VII) with a tin(II)triflate in the presence of a base to give an enolate and then the reaction of the resulting enolate with the compound of the formula (VI) to give the azetidin-2-one derivative of the formula (VIII).

The enolization reaction of the N-propionyl-1,3-thiazoline-2-thione derivative of the formula (VII) with the tin(II)triflate may be carried out usually in a solvent inert in the reaction, such as an ether, i.e., diethyl ether, tetrahydrofuran or the like; a hydrocarbon, i.e., toluene, xylene, cyclohexane or the like; a halogenated hydrocarbon, i.e., dichloromethane, chloroform or the like. Preferably tetrahydrofuran can be used.

Reaction temperatures are not limited to a particular range of temperatures and may vary in a wide range with starting materials to be used or the like. Usually the reaction temperatures may be in a range of relatively low temperatures as low as from approximately $-100°$ C. to about room temperature, preferably from approximately from $-78°$ C. to approximately 0° C.

A quantity of the tin(II)triflate with respect to the compound of the formula (VII) is not critical and may range usually from approximately 1 mole to approximately 2 moles, preferably from 1 to 1.5 moles, of the tin(II)triflate per mole of the compound of the formula (VII).

The enolization reaction above is carried out usually in the presence of the base including, for example, a tertiary amine such as triethylamine, diisopropylethyl amine, 1,4-diazebicyclo-[2,2,2]octane, N-methylmorpholine, N-ethylpiperidine, pyridine or the like. N-Ethylpiperidine is employed advantageously. The base may be used at a rate ranging generally from approximately 1.0 to approximately 3 molar equivalents, preferably from 1.0 to 2 molar equivalents, per mole of the compound of the formula (VII).

The enolization reaction as described above may be completed generally in approximately 5 minutes to approximately 4 hours, thus leading to the formation of the enolate.

After completion of the enolization reaction, the resulting enolate may be used as it is for further reaction with the compound of the formula (VI).

The resulting enolate is then subjected to the alkylation reaction with the compound of the formula (VI). The alkylation reaction may be conducted at temperatures in the range generally from approximately $-100°$ C. to about room temperature, preferably from approximately from $-78°$ C. to approximately $-10°$ C. A quantity of the compound of the formula (VI) is not critical and may vary conveniently in a range generally from approximately 0.5 mole to approximately 5 moles, preferably from 0.5 to 2 moles, per mole of the compound of the formula (VII) used for the enolization.

The alkylation reaction may be carried out under such conditions as have been described above generally for approximately 5 minutes to approximately 5 hours, preferably for 5 minutes to approximately 2 hours.

The enolization and alkylation reactions may be carried out preferably in an inert atmosphere such as in the atmosphere of nitrogen gas or argon gas.

The reaction product obtained by the above reaction is then treated with water. For instance, after completion of the reaction, a phosphate buffer with approximately pH 7 is added, and a mixture is then stirred to be followed by filtration of undissolved materials. After filtration, the compound of the formula (VIII) is separated and purified in conventional manner, such as by means of extraction, recrystallization, chromatography and so on.

The step (b) is a step by which the compound of the formula (IX) may be prepared by reacting the azetidin-2-one derivative of the formula (VIII) obtained by the step (a) above with a magnesium malonate represented by the general formula: $(R^3OOCCH_2CO_2)_2Mg$ in the presence of imidazole.

The reaction is carried out preferably in an inert organic solvent such as, for example, an ether solvent, i.e., ether, tetrahydrofuran, dioxane or the like; a hydrocarbon solvent, i.e., toluene, xylene, cyclohexane or the like; a halogenated hydrocarbon solvent, i.e., dichloromethane, chloroform or the like; acetonitrile and so on. Particularly acetonitrile may be employed conveniently.

Reaction temperatures are not limited strictly to a particular range and may vary in a wide range with starting materials to be used or the like. They may range generally from approximately 0° C. to approximately 100° C., preferably around room temperature.

A quantity of the magnesium malonate with respect to the compound of the formula (VIII) may be about an equimolar amount, and the reaction may be completed in approximately 50 hours, preferably in approximately 20 hours.

The magnesium malonate to be used may include, for example, p-nitrobenzylmagnesium malonate, benzylmagnesium malonate, methylmagnesium malonate and so on. Among them, p-nitrobenzylmagnesium malonate is preferably used.

The step (c) is a step to eliminate a hydroxyl protecting group Z from the compound of the formula (IX) obtained by the step (b) above. The tertiary-butyldimethylsilyl group as the hydroxyl protecting group Z may be eliminated by subjecting the compound of the formula (IX) to acidic hydrolysis in a solvent such as methanol, ethanol, tetrahydrofuran, dioxane or the like in the presence of an acid such as a mineral acid, i.e., hydrochloric acid, sulfuric acid or an organic acid, i.e., acetic acid at temperatures ranging from 0° C. to 100° C. for reaction periods ranging from 0.5 to 18 hours.

The above step may yield the compound represented by the formula (X) in a quantitative amount.

The step (d) is a step by which the diazo compound of the formula (XI) may be prepared by treating the compound of the formula (X) obtainable by the above step (c) with an azide compound in the presence of a base in such an inert organic sovent as have been enumerated for the step (b) above.

The azide compound to be used in the step (d) may include, for example, p-carboxylbenzenesulfonyl azide, toluenesulfonyl azide, methanesulfonyl azide, dodecylbenzenesulfonyl azide or the like. The base to be used therein may include, for example, triethylamine, pyridine, diethylamine or the like.

The reaction may be carried out, for instance, by adding p-toluenesulfonyl azide in acetonitrile preferably in the presence of triethylamine at 0° C. to 100° C., preferably at room temperature for 1 to 50 hours. This reaction produces the diazo compound represented by the formula (XI) with high yield.

The step (e) is a step by which the diazo compound of the formula (XI) obtained by the step (d) above may be cyclized to give the compound of the formula (XII). This step may be carried out preferably in an inert solvent such as benzene, toluene, tetrahydrofuran, cyclohexane, ethyl acetate, dichloromethane or the like, preferably in toluene, at temperatures ranging from 25° C. to 110° C. for 1 to 5 hours in the presence of a metal catalyst such as a metal carboxylate compound including, for example, bis(acetylacetonato)Cu(II), $CuSO_4$, copper powder, $Rh_2(OCOCH_3)_4$, rhodium octanoate, $Pb(OCOCH_3)_4$ or the like. As an alternative procedure, the above cyclization step may be carried out by subjecting the compound of the formula (XI) to irradiation from a light source through a Pyrex filter (its wavelength being larger than 300 nm) in a solvent such as benzene, diethyl ether or the like at 0° C. to 250° C. for 0.5 to 2 hours.

The step (f) produces the compound of the formula (II) by reacting the compound of the formula (XII) obtainable by the step (e) with a reactive derivative of an acid represented by the formula: RaOH. The reactive acid derivative may include, for example, an acid anhydride such as acetic acid anhydride, methanesulfonic acid anhydride, p-toluenesulfonic acid anhydride, p-nitrobenzenesulfonic acid anhydride, 2,4,6-triisopropylbenzenesulfonic acid anhydride, trifluoromethanesulfonic acid anhydride or the like or an acid halide such as an acid chloride, i.e., acetyl chloride, propionyl chloride, diphenylphosphoric chloride, toluenesulfonyl chloride, p-bromobenzenesulfonyl chloride or the like. Diphenylphosphoric chloride ($R^a$=diphenylphosphoryl group) is particularly preferred.

The reaction of the compound of the formula (XII) with the reactive acid derivative may be carried out, for example, in a manner similar to a conventional acylation reaction in an inert solvent such as methylene chloride, acetonitrile, dimethylformamide or the like, conveniently in the presence of a base such as diisopropylethyl amine, triethylamine, 4-dimethylaminopyridine or the like at temperatures ranging from −20° C. to 40° C. for approximately 30 minutes to approximately 4 hours.

The reaction consisting of a series of the steps as have been described above provides the compound represented by the formula (II) with a highly spatial selectivity and with such a spatial arrangement that the methyl group at the 1-position of the carbapenem skeleton is arranged in the R configuration, the sustituent at the 5-position thereof is in the R configuration, and the substituent and the hydroxymethyl group each at the 6-position thereof are in the S and R configurations, respectively.

The compound represented by the formula (II) is then reacted with a mercapto reagent represented by the formula (III) to give the compound represented by the formula (IV).

The reaction of the compound of the formula (II) with the mercapto reagent of the formula (III) may be carried out, for instance, by reacting the compound of the formula (II) with the mercapto reagent of the formula (III) in an excess amount ranging from about equimolar amount to approximately 1.5 molar amount in an appropriate solvent such as tetrahydrofuran, dichloromethane, dioxane, dimethylformamide, dimethylsulfoxide, acetonitrile, hexamethylene phosphoramide or the like, preferably in the presence of a base such as sodium hydrogen carbonate, potassium carbonate, triethylamine, diisopropylethyl amine or the like at a temperature range from approximately −40° C. to approximately 25° C. for approximately 30 minutes to approximately 24 hours.

The reaction described above provides the carbapenem compound represented by the formula (IV) in which the carboxyl group at the 3-position thereof is protected by the carboxyl protecting group $R^3$ and the substituent at 2-position thereof is protected by the amino protecting group $R^b$. The removal of the protecting groups $R^3$ and $R^b$ may be made by a per se known reaction for removing a protective group, such as solvolysis or hydrogenolysis. In a typical reaction, the compound represented by the formula (IV) may be treated, for instance, in a mixture of solvents such as tetrahydrofuran-water, tetrahydrofuran-ethanol-water, dioxane-water, dioxane-ethanol-water, n-butanol-water or the like containing morpholino-propane sulfonic acid-sodium hydroxide buffer solution (pH 7), a phosphate buffer solution (pH 7), dipotassium phosphate, sodium bicarbonate or the like, using hydrogen under 1 to 4 atmospheric pressures, in the presence of a catalyst for hydrogenation such as platinum oxide, palladium-activated carbon or palladium hydroxide-activated carbon at temperatures ranging from approximately 0° C. to approximately 50° C. for approximately 0.25 to approximately 4 hours.

In accordance with the above steps, (1R,5S,6S)-2-[4-pyrazolidinyl]thio-6-[(R)-1-hydroxyethyl]-1-methyl-carbapenem-3-carboxylic acid represented by the formula (V) is produced. Then, this compound of the formula (V) is converted to the present carbapenem compound of the formula (I) by reacting with alkyl imidoformate. The reaction with the compound of the formula (V) with alkyl imidoforamte may be conducted by dissolving the compound of the formula (V) in a week basic medium, for instance, in the basic medium (pH 8.5) consisting of a phosphate buffer(pH 7.5) and 1N-sodium hydroxide solution and causind a ethyl formimidate on the resulting solution.

The mercapto reagent of the formula (III) to be employed in the process described above may be prepared in a manner as indicated in Reaction Scheme B blow.

REACTION SCHEME B

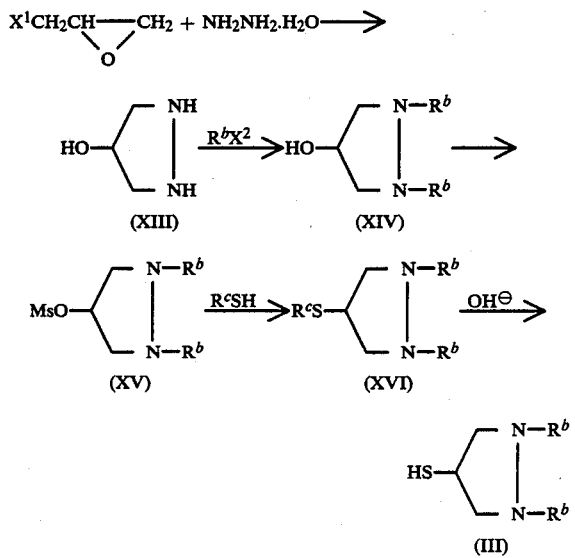

wherein $R^b$ has the same meaning as above; $X^1$ and $X^2$ are halogen atoms as chlorine atoms; Ms is methansulfonyl groups; and $R^c$ is a lower acyl group such as acetyl, propionyl, butyryl group.

4-Hydroxyprazoline of the formula (XIII) prepared by the reaction between hydrazine hydrate and epihalohydrin is treated with the acylation reagent of the formula $R^bX^2$ to give the compound of the formula (XIV). Then, the resulting compound of the formula (XIV) is converted to the compound of the formula (XV) by methansulfonylation, and the compound of the formula (XV) is reacted with the compound of the formula $R^cSH$ such as thiolacetic acid to obtain the compound of the formula (XVI). Finally, the resulting compound of the formula (XVI) is converted to the objective mercapto reagent of the formula (III) by reacting with alkali metal alkoxide such as sodium methoxide, sodium ethoxide or the like.

The compound of the present invention respresented by the formula (I) may be converted to a pharmaceutically acceptable salt therof by usually manner. Such a salt may be, for example, an alkali metal salt such as sodium, potassium salt thereof; an amino acid salt such as arginine, ornithine, lysine salt thereof; and an ammonium salt such as diethanolammonium, triethanolammonium salt thereof, but the sodium or potassium salt thereof may be more preferable described above.

The objective compounds of the formula (I) in accordance with the present invention represented by (1R,5S,6S)-2-(5H-pyrazolo[1,2-a]triazolinium-6-yl)thio-6-[(R)-1-hydroxyethyl]-1-methyl-carbapenem-3-carboxylic acids are novel compounds that are not disclosed specifically in the above-mentioned publication and that are extremely stable against dehydropeptidase (DHP) known as a kidney enzyme and superior in antibacterial activities. The remarkably high antibacterial activities and stability against the kidney DHP of the compound of the formula (I) according to the present invention have been determined by biological tests as will be described below.

I: Antibacterial Tests

Test Procedures:

The antibacterial activities were tested by an agar plate dilution method in accordance with the standard method of the Japanese Chemotherapy Society (Chemotherapy, Vol. 29, 76–79 (1981)).

A Mueller-Hinton (MH) agar liquid medium of a test microorganism was cultured overnight at 37° C. and the resultant culture medium was diluted with a buffered saline gelatin (BSG) solution to contain approximately $10^8$ cells of the test microorganims per milliliter, and then the diluted solution was inoculated with a microplanter at the rate of approximately 5 microliters on a MH agar medium containing a test compound. This medium was then incubated at 37° C. for 18 hours. The minimum inhibitory concentration (MIC) is determined as a minimum concentration in which no test microorganism could grow. It is noted here that the test organisms used were all standard strains.

Results:

Table 1 shows the test results. It is to be noted here that the test compound used therein was the compound (15) obtained in Example No. 6. As control compounds were used ones clinically employed widely, viz., cefazolin (CEZ) as a cephalosporin compound, and imipenem as a carbapenem compound.

TABLE 1

| | MIC (μg/ml) Test Compounds | | |
|---|---|---|---|
| Test Organisms | CEZ | Imipenem | Compd. (15) |
| Staphylococcus aureus FDA 209P JC-1 | 0.2 | 0.025 | 0.05 |
| Staphylococcus aureus Terajima | 0.05 | <0.006 | 0.025 |
| Staphylococcus aureus MS352 | 0.1 | 0.013 | 0.1 |
| Streptococcus pyogenes Cook | 0.1 | <0.006 | 0.025 |
| Micrococcus luteus ATCC9341 | 0.39 | 0.025 | 0.1 |
| Bacillus subtilis ATCC6633 | 0.1 | 0.025 | 0.1 |
| Escherichia coli NIHJ JC-2 | 0.78 | 0.1 | 0.05 |
| Escherichia coli K12 C600 | 0.78 | 3.13 | 0.2 |
| Enterobacter aerougenes ATCC13048 | >100 | 3.13 | 0.39 |
| Enterobacter cloacae 963 | >100 | 0.2 | 0.1 |
| Klebsiella pneumoniae PCI-602 | 0.78 | 0.39 | 0.05 |
| Salmonella typhimurium IID971 | 0.78 | 0.39 | 0.1 |
| Salmonella typhi 901 | 0.78 | 0.1 | 0.025 |
| Salmonella paratyphi 1015 | 1.56 | 1.56 | 0.39 |
| Salmonella schottmuelleri 8006 | 0.78 | 0.78 | 0.2 |
| Salmonella enteritidis G14 | 0.78 | 0.78 | 0.2 |
| Serratia marcescens IAM1184 | >100 | 0.39 | 0.2 |
| Morganella morganii IFO3848 | 25 | 0.39 | 0.1 |
| Proteus mirabilis IFO3849 | 6.25 | 6.25 | 0.39 |
| Proteus vulgaris OX-19 | 6.25 | 0.78 | 0.025 |
| Proteus vulgaris HX-19 | 8.25 | 0.78 | 0.1 |

TABLE 1-continued

| Test Organisms | MIC (μg/ml) Test Compounds | | |
|---|---|---|---|
| | CEZ | Imipenem | Compd. (15) |
| *Providencia rettgeri* IFO 3850 | 12.5 | 0.78 | 0.2 |
| *Pseudomonas aeruginosa* IFO 3445 | >100 | 0.78 | 0.78 |
| *Pseudomonas aeruginosa* NCTC 10490 | >100 | 0.78 | 0.78 |

From the foregoing results, it is apparent that the carbapenem compound according to the present invention has superior antibacterial activities.

II: Antibacterial Activities against Clinically Isolated β-Lactamase (Cephalosporinase) Producing Strains Test Procedures:

The antibacterial activities against clinically isolated β-lactamase producing strains have been tested by the agar plate dilution method in accordance with the standard method of the Japanese Chemotherapy Society (Chemotherapy, Vol. 29, 76–79 (1981)). A solution of a cephalosporinase producing strain stored by Episome Research Institute, which was prepared by incubating the strain in a sensitivity test broth (STB; product of Nissui K.K.) for 18 hours, was diluted with a fresh STB solution to contain 105 cells per milliliter and the diluted solution was then inoculated as spots with a microplanter on a sensitivity disk agar-N (SDA; product of Nissui K.K.) containing a test compound. The disk agar was then incubated for 18 to 20 hours. A minimum inhibitory concentration was determined as a minimum concentration in which the test microorganism had no longer grown after a 18 to 20 hour incubation.

Results:

Table 2 shows the test results. It is to be noted here that the test compound used therein was the compound (15) obtained in Example No. 6. As control compounds were used ceftazidime (CAZ) as a cephalosporin compound, and imipenem as a carbapenem compound, both being recognized as having remarkably high antibacterial activities against the test strains and being widely employed clinically.

TABLE 2

MINIMUM INHIBITORY CONCENTRATIONS (MIC)

| Test Organisms | MIC (μg/ml) Test Compounds | | |
|---|---|---|---|
| | CDZ | Imipenem | Compd. (15) |
| *Providencia rettgeri* GN 5284 | 0.2 | 0.39 | 0.2 |
| *Providencia rettgeri* GN 4430 | 0.2 | 0.39 | 0.2 |
| *Providencia rettgeri* GN 4762 | 0.78 | 0.39 | 0.2 |
| *Escherichia coli* GN 5482 | 0.78 | 0.1 | 0.025 |
| *Escherichia coli* No. 1501 | 0.2 | 0.1 | 0.025 |
| *Escherichia coli* No. 96 | 0.78 | 0.1 | 0.025 |
| *Enterobacter cloacae* GN 7471 | 3.13 | 0.2 | 0.1 |
| *Enterobacter cloacae* GN 7467 | 3.13 | 0.78 | 1.56 |
| *Enterobacter cloacae* GN 5797 | 0.39 | 0.39 | 0.1 |
| *Proteus morganii* GN 5407 | 0.39 | 3.13 | 1.56 |
| *Proteus morganii* GN 5307 | 0.2 | 0.78 | 0.39 |
| *Proteus morganii* GN 5375 | 0.2 | 3.13 | 1.56 |
| *Proteus vulgaris* GN 76 | 0.1 | 3.13 | 1.56 |
| *Proteus vulgaris* GN 7919 | 3.13 | 0.39 | 1.56 |
| *Proteus vulgaris* GN 4413 | 0.2 | 6.25 | 1.56 |
| *Pseudomonas aeruginosa* GN 918 | 6.25 | 0.78 | 1.56 |
| *Pseudomonas aeruginosa* GN 10362 | 3.13 | 0.78 | 1.56 |
| *Pseudomonas aeruginosa* GN 10367 | 3.13 | 1.56 | 1.56 |
| *Serratia marcescens* GN 10857 | 0.78 | 3.13 | 1.56 |

TABLE 2-continued

MINIMUM INHIBITORY CONCENTRATIONS (MIC)

| Test Organisms | MIC (μg/ml) Test Compounds | | |
|---|---|---|---|
| | CDZ | Imipenem | Compd. (15) |
| *Serratia marcescens* L-65 | 0.2 | 0.39 | 0.2 |
| *Serratia marcescens* L-82 | 0.39 | 0.2 | 0.1 |
| *Citrobactor freundii* GN 346 | 25 | 0.39 | 0.78 |
| *Citrobactor freundii* GN 7391 | >100 | 0.78 | 0.78 |
| *Pseudomonas cepacia* GN 11164 | 0.78 | 3.13 | 0.39 |
| *Klebsiella oxytoca* GN 10650 | 0.2 | 0.2 | 0.1 |

It has been found from the above results that the carbapenem compound according to the present invention had the antibacterial activities against *P. aeruginosa* and *P. cepacia* belonging to Pseudomonadaceae as high as imipenem and particularly higher than CAZ having anti-Pseudomonas activities.

It has been found further that the carbapenem compound according thereto had the activities against enteric bacteria excluding the genus Proteus as high as imipenem and superior to CAZ.

III. Sensitivity Tests against Clinical Isolates

1. *P. aeruginosa* resistant strains (1) Strains of Test Organisms:

Fifty-four strains of *P. aeruginosa* demonstrating a resistance against the following agents in such concentrations as having been indicated between the following parentheses were employed for sensitivity tests against clinical isolates. It is noted here that the 54 strains have been chosen because there have been the strains in duplicate with the agents.

| Ceftazidime (CAZ) | (25 to 100 μg/ml) | 21 strains |
|---|---|---|
| Cefsulodine (CFS) | (25 to <100 μg/ml) | 23 strains |
| Piperacilin (PIPC) | (25 to <100 μg/ml) | 15 strains |
| Gentamycin (GM) | (25 to <100 μg/ml) | 21 strains |
| Amikacin (AMK) | (25 to <100 μg/ml) | 26 strains |
| Ofloxacin (OFLX) | (25 to <100 μg/ml) | 4 strains |

(2) Test Procedures:

The test procedures were based on the agar plate dilution method in accordance with the standard method of the Japanese Chemotherapy Society. A minimum inhibitory concentration (MIC) was determined in substantially the same manner as the test procedures II above using the 54 strains of *P. aeruginosa* having an anti-Pseudomonas resistance.

(3) Results:

The compound (15) obtained in Example 6, on the one hand, was found to demonstrate the antibacterial activities to inhibit the growth of approximately 98% of the test microorganisms in a concentration of 6.25 μg/ml and all the test microorganisms in a concentration of 12.5 μg/ml.

The imipenem, on the other hand, was found to inhibit the growth of approximately 98% of the test microorganisms in a concentration of 6.25 μg/ml and all the test microorganism in a concentration of 12.5 μg/ml.

2. *C. freundii* resistant strains (1) Strains of the Test Organisms:

Twenty-strsins of *C. freundii* demostraing a resistance again st the following agent as same manner descrived above Test 1.

Cefixime (CFIX) (50 to >100 μg/ml)
Cefotaxime (CTX) (50 to >100 μg/ml)

(2) Test Rrocedures:

The tests were carried out in the same manner as descrived above Test 1.

(3) Results:

The compound (15) obtained in Example 6 was found to demonstrate the antibacterial activities to inhibit the growth of approximately 98% of the test microorganisms in a concentration of 0.78 μg/ml and all the test microorganisms in a concentration of 1.56 μg/ml.

The imipenem, on the other hand, was found to inhibit the growth of approximately 90% of the test microorganisms in a concentration of 0.78 μg/ml and all the test microorganisms in a concentration of 1.56 μg/ml.

From the above results, it has been found apparent that the compound according to the present invention is superior in the antibacterial activities to imipenem.

IV. Stability Test against Kidney Dehydropeptidase:

1. Materials:

(1) Swine Kidney Dehydropeptidase-I (DHP-I):

The swine kidney (8 kg) was homogenized and an enzyme protein was allowed to precipitate. After a connective lipid was removed with acetone, the resultant material was made soluble by treatment with butanol and purified in the order by the ammonium sulfate fraction method, thereby producing DHP-I enzyme from a 75% ammonium sulfate fraction.

The DHP-I enzyme was then adjusted to give an enzyme concentration of 25 mg/10 ml (phosphate buffer, pH 7.1), and divided into 1 ml portions. The portions were frozen and stored at −40° C. or less until use.

(2) Test Compound:

As a test compound was used the compound (15) obtained in Example 6 that follows.

The test compound was adjusted in situ to give the concentration of 117 μM with a 50 mM sodium phosphate buffer solution (pH=7.1).

As control compounds were employed glycyl dehydrophenylalanine (Gl-dh-Ph) and imipenem, and they were adjusted in situ each to give the concentration of 117 μM with the same sodium phosphate buffer solution.

2. Method:

(1) Measurement for Hydrolysis Activity against DHP-I Enzyme Substrate by Late Assay:

To 1.2 ml of a 50 mM sodium phosphate buffer solution (substrate) containing 117 μM of each of Gh-dh-Ph and imipenem as the control compounds was added 0.2 ml of the DHP-I enzyme solution (25 mg/10 ml) prepared above in the final substrate concentration of 100 μM. The solution was then incubated at 37° C. for 10 minutes. An initial velocity of hydrolysis of the substrate was measured from a decrease in absorbency at a particular λmax of each of the substrates.

A blank test was conducted in substantially the same manner as above by adding 0.2 ml of the sodium phosphate buffer solution (pH 7.1) to 1.2 ml of the above substrate.

(2) Measurement for Stability of Test Compounds against DHP-I by High Performance Liquid Chromatography Method (HPLC):

The test compound according to the present invention and the control compounds have been treated in substantially the same manner as (1) above. The incubation, however, was conducted at 37° C. for 4.5 hours or for 24 hours. A degree of the hydrolysis of the compounds each after the test periods of time was measured by the HPLC method.

3. Results:

The initial velocity of hydrolysis of each of the substrates against DHP-I by the late assay was found as follows:

Gl-dh-Ph: 17.4 μM/minute
Imipenem: 0.56 μM/minute

Table 3 below shows measurement results on stability of the compound according to the present invention and imipenem against DHP-I.

TABLE 3

DEGREES OF HYDROLYSIS BY DHP-I
(Method: HPLC; Substrate Concentration: 100 μM; Unit: μM)

| Incubation Conditions | Test Compounds | |
|---|---|---|
| | Imipenem | Compound (15) |
| 37° C., 4.5 hours | 77.6 | 2.8 |
| 37° C., 24 hours | * | 2.9 |

*After 24 hours at 37° C., it has been found that most or all imipenem has been decomposed and nothing remained was detected.

From the stability test results against DHP-I, it is found apparent that the carbapenem compound according to the present invention was stabler by approximately twenty-eight times than that of imipenem.

V. Toxicity:

Toxicological studies have been carried out using a group of 10 male mice of CrjCD(SD) type weighing from 20 to 23 grams. A solution containing the carbapenem compound (15) of the present invention obtained by Example 6 was administered subcutaneously to the mice and subjected to observations for one week.

The results have revealed that a group of the mice to which the carbapenem compound (15) of the present invention had been administered in the amount of 500 mg/kg were alive without any abnormal observations.

As have been described above, the carbapenem compounds according to the present invention demonstrate a wider scope of antibacterial spectra compared to conventional cephalosporin compounds and remarkable antibacterial activities comparative to imipenem as well as an overwhelmingly higher resistance against DHP compared to imipenem. The carbapenem compounds according to the present invention further possess superior antibacterial activities against clinically isolated strains and present favorable effects on infection preventive tests on mice against various organisms.

Therefore, the carbapenem compounds of the formula (I) according to the present invention permit a single administration without a combination with any other compounds and without a risk of any side effect that might be caused to arise in combination with a DHP inhibitor, unlike imipenem that was led for the first time to a practically useful antibacterial agent in combination with cilastatin acting as a DHP inhibitor. The carbapenem compounds are accordingly extremely useful as antibacterial agents for therapy and prevention of infectious diseases from various pathogenic organisms.

The carbapenem compound of the formula (I) according to the present invention may be administered as an antibacterial agent to the human being and other mammarian animals in the form of a pharmaceutically acceptable composition containing an antibacterially effective amount thereof. A quantity of administration may vary in a wide range with ages of patients, weights, patient conditions, forms or routes of administration, patient's diagnoses or the like and may be orally, parenterally or topically administered, usually, to adult patients once or in several installments per day in a standard daily dose range from approximately 200 to approximately 3,000 mg.

The pharmaceutically acceptable composition of the carbapenem compound of the formula (I) according to the present invention may cantain an inorganic or organic, solid or liquid carrier or diluent, which is conventionally used for preparations of medicines, particularly antibiotic preparations, such as an excipient, e.g., starch, lactose, white sugar, crystalline cellulose, calcium hydrogen phosphate or the like; a binder, e.g., acacia, hydroxypropyl cellulose, alginic acid, gelatin, polyvinyl pyrolidone or the like; a lubricant, e.g., stearic acid, magnesium stearate, calcium stearate, talc, hydrogenated plant oil or the like; a disintegrator, e.g., modified starch, calcium carboxylmethyl cellulose, low substituted hydroxypropyl cellulose or the like; or a dissolution aid, e.g., a non-ionic surface active agent, an anionic surface active agent or the like, and may be prepared into forms suitable for oral, parenteral or topical administration. The formulations for oral administration may include solid preparations such as tablets, coatings, capsules, troches, powders, fine powders, granules, dry syrups or the like or liquid preparations such as syrups or the like; the formulations for parenteral administration may include, for example, injectable solutions, drip-feed solutions, depositories or the like; and the formulations for topical administration may include, for example, ointments, tinctures, creams, gels or the like. These formulations may be formed by procedures known per se to those skilled in the art in the field of pharmaceutical formulations.

The carbapenem compounds of the formula (I) according to the present invention are suitably administered in the form of parenteral formulations, particularly in the form of injectable solutions.

The production of the carbapenem compounds of the formula (I) according to the present invention will be described more in detail by way of working examples.

In the following description, the following symbols are used to have the particular meanings:
ph: phenyl group
PNB: p-nitrobenzyl group
PNZ: p-nitrobenzyloxycarbonyl group

tertiary-butyldimethylsilyl group
Ac: acetyl group
Et: ethyl group

EXAMPLE 1

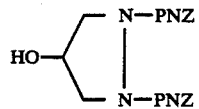 (Compound 1)

To 15 g of hydrazine monohydratre in 50 ml flask was added dropwise, 9.3 g of epichlorohydrine at 0° C. for 1 hour and after dropwise, the reactione mixture was stirred for 2 hours at same temperature. After removal of the exess hydrazin under reduced pressure, 300 ml of a saturated sodium bicarbonate solution and 200 ml of tetrahydrofuran were added to the residue. To this solution was added dropwise a solution of 43 g of p-nitrobenzyloxycarbonyl chloride in 150 ml of tetrahydrofuran, hten the reaction mixture was stirred for 2 hours. After reaction, 200 ml of ethyl acetate was added to the reaction mixture, the organic layer was seoarated and water layer was extracted with 100 ml of ethyl acetate. The combined organic layer was washed with a saturated sodium chloride aqueous solution and dried over sodium sulfate. The soluvent was removed and 500 ml of chloroform was added to the residue then the resulting solution was stored in the refrigerater to give a precipitate. After removal of the precipitate, the soluvent was removed and the residue was purified using silica gel colum chromatography (dichloromethane) to give 16.7 g of the Compound 1.

NMR (CDCl$_3$) δ: 8.15 (4H, d), 7.48 (4H, d), 5.4–5.0 (1H, m), 5.37 (4H, s), 4.4–3.2 (4H, m).

EXAMPLE 2

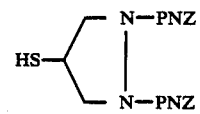 (Compound 2)

(a) To a solution fo 16.6 g of the Compound (1) obtained by Example 1 and 5.6 g of triethylamine in 200 ml of dichloromethane was added dropwise a solution of 6.42 g of methansulufonyl chloride in 20 ml of dichloromethane at 0° C. and the reaction mixture was stirred for 15 minutes at room temperature. After reaction, the organic layer was washed with 200 ml of water, 200 ml of a satulated sodium bicarbonate solution and 200 ml of a saturated sodium chloride solution and then dried over sodium sulfate. The solvent was removed to give 16.6 g of pale yallowish powder.

(b) A solution of 9.6 g of the above powder, 3.13 g of potassium acetate and 250 ml of acetone was refluxed for 2 hours. After addition of 50 ml of water, the reaction solvent was removed and the resulting residue was extracted with ethyl acetate. The organic layer was washed with water, dried over and removed. The resulting residue was purified using silica gel colum chromatography by chloroform as an eluent to give 5.9 g of pwder.

(c) To a solution of 13.6 g of the above powder, 145 g of tetrahydrofuran and 145 ml of methanol was added 12.3 ml of 4% sodium methoxide-methanol solution at 0° C. and the reaction mixture was stirred for 5 minutes. After reaction, 1N-hydrogen chloride solution was added to the reaction mixture and the resulting acidic solution was extracted with ethyl acetate. After washing and drying, the solvent was removed to give 11.9 g (63%) of the Compound (2) as pale brownish powder.

NMR (CDCl$_3$) δ: 8.17 (4H, d), 7.48 (4H, d), 5.28 (4H, g), 4.5–3.2 (4H, m).

EXAMPLE 3

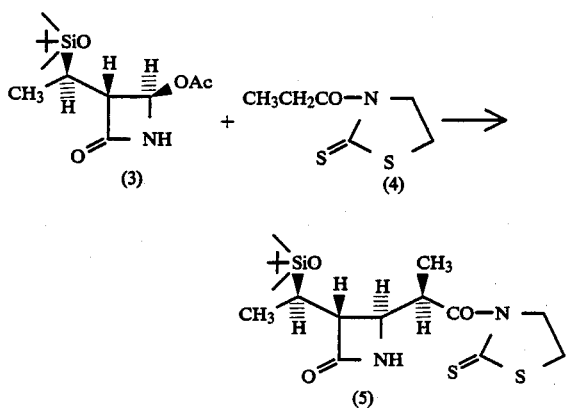

Tin triflate (3.712 g) was dissolved in 10 ml of anhydrous tetrahydrofuran under nitrogen gas streams, and the resulting solution was cooled to 0° C. To this solution was added 1.3 ml of N-ethylpiperidine and a solution of 1.2 g of the Compound (4) above in 7 ml of anhydrous tetrahydrofuran, and the mixture was stirred for 2 hours at the same temperature. To this was added a solution of 1.42 g of the Compound (3) in 2 ml of anhydrous tetrahydrofuran, and the resultant mixture was stirred for 1 hour. After the completion of the reaction, 100 ml of chloroform was added and the mixture was washed with a 10% citric acid aqueous solution. The organic layer separated was then dried over MgSO4 and the solvent was removed leaving the residue that was in turn purified by a silica gel column chromatography with a n-hexane:ethyl acetate (2 - 1:1) mixture to give 1.93 g (97%) of the Compound (5) as a yellow solid material.

NMR (CDCl3) δ: 0.07 (6H, s), 0.88 (9H, s), 1.21 (3H, d), 1.26 (3H, d), 3.30 (1H, dd), 3.28 (2H, t), 3.94 (1H, dd), 4.55 (2H, t), 6.24 (1H, bs).

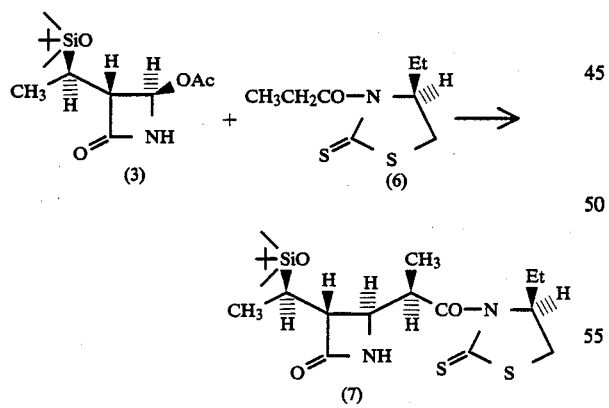

Tin triflate (57.0 g) was dissolved in 164 ml of anhydrous tetrahydrofuran under nitrogen gas streams, and the resulting solution was cooled to 0° C. To this solution was added 19.9 ml of N-ethylpiperidine and a solution of 21.71 g of the Compound (6) above in 123 ml of anhydrous tetrahydrofuran and the mixture was stirred for 1.5 hours at the same temperature. To this was added a solution of 1.42 g of the Compound (3) in 123 ml of anhydrous tetrahydrofuran, and the resultant mixture was stirred for 1 hour. After the completion of the reaction, chloroform was added and the mixture was washed with a 10% citric acid aqueous solution and a sodium chloride aqueous solution. The organic solution separated was then dried over MgSO4 and the solvent was removed leaving the residue that was in turn purified by a silica gel column chromatography with n-hexane:ethyl acetate (2:1) to give 33.57 g (98%) of the Compound (7) as a yellow solid material, m.p. 85.5°-86.5° C.

NMR (CDCl3) δ: 0.07 (6H, s), 0.90 (9H, s), 1.00 (3H, t), 1.23 (3H, d), 1.26 (3H, d), 2.90 (1H, dd), 6.10 (1H, bs). $[\alpha]_{D25} = +233.9°$ C. (C=0.77, CHCl3).

Compound (7)⟶ (C)

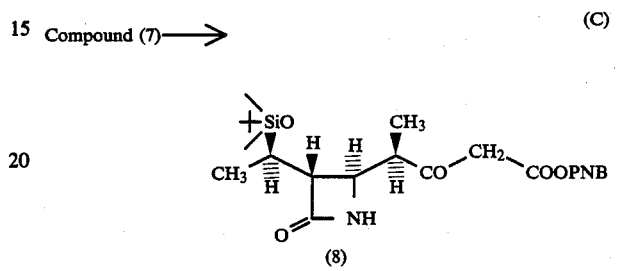

To a solution of 30.66 g of the Compound (7) obtained in the step (B) above in 740 ml of anhydrous acetonitrile was added 12.13 g of imidazole, and the mixture was stirred under nitrogen gas streams at room temperature for 5.5 hours. To this was added 53.39 g of Mg(O2CCH2CO2PNB)2, and the mixture was stirred overnight at 60° C. The resultant reaction mixture was condensed under reduced pressures to 200 ml and 1 liter of ethyl acetate was added thereto. The organic layer separated was washed with a 1N-HCl aqueous solution, a 5% NaHCO3 aqueous solution and a sodium chloride aqueous solution in this order. After dried over MgSO4, the solvent was removed and the residue was purified using a column chromatography with 800 g of silica gel, yielding 37.47 g of the Compound (8) as a colorless oily material.

NMR (CDCl3) δ: 0.06 (6H, s), 0.87 (9H, s), 1.16 (3H, d), 1.20 (3H, d), 3.63 (2H, s), 5.27 (2H, s), 5.92 (1H, bs), 7.56, 8.24 (4H aromatic ring proton).

The Compound (8) obtained above was continued to be used in the following step (D) without further purification.

Compound (8)⟶ (D)

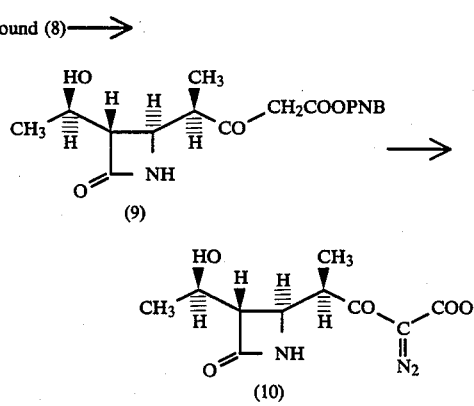

To 37.47 g of the Compound (8) obtained in the step (C) above in 392 ml of methanol solution was added 19.6 ml of concentrated HCl, and the mixture was stirred at room temperature for 1.5 hours. The reaction mixture was condensed to approximately 100 ml, and 800 ml of ethyl acetate was added. After the mixture was washed with water and then with a sodium chloride aqueous solution, it was then dried over MgSO$_4$ and the solvent was removed under reduced pressures, yielding the Compound (9) as a colorless oily material.

NMR (CDCl$_3$) δ: 1.25 (3H, d), 1.30 (3H, d), 2.90 (2H, m), 3.65 (2H, s), 3.83 (1H, m), 4.15 (1H, m), 5.27 (2H, s), 6.03 (1H, bs), 7.55, 8.27 (4H, aromatic ring proton).

The Compound (9) was then dissolved in 408 ml of anhydrous acetonitrile, and 36.31 g of dodecylbenzyl-sulfonyl azide and 13.8 ml of triethylamine were added. After the mixture was stirred at room temperature for 20 minutes, the solvent was removed leaving the residue that was in turn purified by means of column chromatography with 800 g of silica gel using chloroform:acetone (2:1) to give 21.57 g (as total yields of the Compounds (B), (C) and (D)) of the Compound (10) as a colorless oily material.

IR (CHCl$_3$) cm$^{-1}$: 2150, 1720, 1650.

NMR (CDCl$_3$) δ: 1.23 (3H, d), 1.30 (3H, d), 2.92 (1H, m), 3.50–4.30 (3H, m), 5.38 (2H, s), 6.40 (1H, bs), 7.57, 8.30 (4H, aromatic ring proton).

[α]$_{D21}$=−41.6° (C=3.1, CH$_2$Cl$_2$).

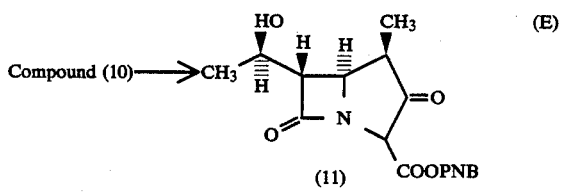

(E)

In 134 ml of ethyl acetate was dissolved 21.57 g of the Compound (10) obtained in the step (D) above, and 0.065 g of rhodium octanoate was added. The solution was stirred at 80° C. for 0.5 hour and the solvent was removed, leaving the residue that was in turn dried to give the Compound (11) as a solid material.

IR (CHCl$_3$) cm$^{-1}$: 2950, 2925, 1860, 1830.

NMR (CDCl$_3$) δ: 1.22 (3H, d, J=8.0 Hz) 1.37 (3H, d, J=6.0 Hz) 2.40 (1H, bs) 2.83 (1H, q, J=8.0 Hz) 3.28 (1H, d, d) 4.00–4.50 (2H, m) 4.75 (1H, s) 5.28 and 5.39 (2H, ABq, J=12 Hz) 7.58, 8.24 (4H, aromatic ring proton).

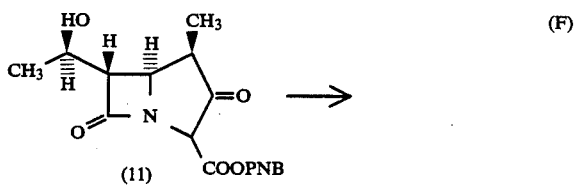

(F)

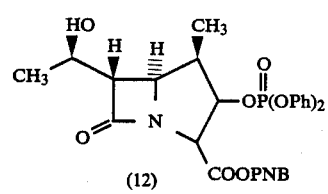

To a solution of 186 mg of the Compound (11) obtained in the step (E) in 2 ml of anhydrous acetonitrile were added 0.11 ml of diphenylphosphoric chloride and 0.09 ml of diisopropylethyl amine under cooling with ice, and the mixture was stirred for 0.5 hour at the same temperature. After the reaction mixture was condensed, the residue was purified using a silica gel column, yielding 252 mg of the Compound (12) as a white solid material.

NMR (CDCl$_3$) δ: 1.24 (3H, d), 1.34 (3H, d), 3.30 (1H, q), 3.52 (1H, m), 4.10–4.40 (2H, m), 5.20 and 5.35 (2H, q), 7.29 (10H, m), 7.58 and 8.18 (4H, d).

EXAMPLE 4

Compound (12)⟶

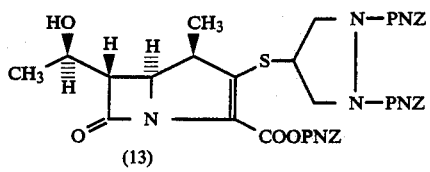

To a solution of 476 mg of the Compound (12) obtained in Example 3 in anhydrous acetonitrile was added a solution of 460 mg of the Compound (2) obtained in Example 2 and 0.17 ml of diisopropylethyl amine, and the mixture was stirred for 40 minutes under nitrogen atmosphere. Removal of the solvent left the reside that was in turn purified by means of silica gel column chromatography chloroform:acetone=3:1), yielding 667 mg (100%) of the Compound (13).

NMR (CDCl$_3$) δ: 1.24 (3H, d, J=6.0 Hz), 1.35 (3H, d, J=6.0 Hz), 3.2–4.4 (9H, m), 5.16 (1H, d, J=15.0 Hz), 5.26 (2H, s), 5.47 (1H, d, J=15.0 Hz), 7.3–7.7 (6H, m), 8.05–8.3 (6H, m).

EXAMPLE 5

Compound (13)⟶

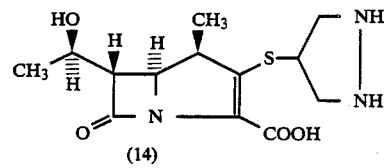

To a solution of 667 mg of the Compound (13) in 7 ml of tetrahydrofuran and 7 ml of water was added 120 mg of platium oxide, and the catalytic hydrogenation was carried out at room temperature for 1 hour under 3.0 atmospheric pressures. After removal of the catalyst, the solvent was removed to give 192 mg (74.0%) of the Compound (14) after lyophilization.

IR (KBr) cm$^{-1}$: 1750.

NMR (D$_2$O—CD$_3$OD) δ: 1.23 (3H, d, J=6.0 Hz), 1.40 (3H, d, J=7.0 Hz), 3.3–4.4 (9H, m).

EXAMPLE 6

Compound (14)⟶

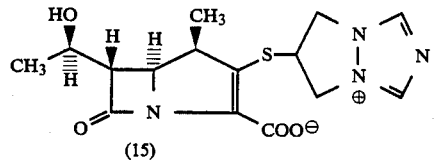

192 mg of the Compound (14) was dissolved in 15 ml of phosphate buffer solution (pH 7.0), and a pH of the solution was adjusted to 8.5 by 1N sodium hydroxide solution. To this solution was added 570 mg of ethyl formimidate hydrochloride, and the reaction mixture was stirred for 1 hour under ice-cooling. After the pH of the reactin mixture was adjusted to 7.0, the solvent was removed and the resulting residue was lyophilized. The resulting powder was purified using HP-40 column (water, 3% acetone-water) to give 76 mg (33.8%) of 6-[(R)-1-hydroxyethyl]-1-methyl-2-(5H-pyrazolo[1,2-a]triazolinium-6-yl)thio-cabapenem-3-carboxylic acid (Compound 15) after lyophilization.

NMR (D$_2$O) δ: 1.32 (3H, d, J=6.0 Hz), 1.40 (3H, d, J=6.0 Hz), 3.3-4.4 (9H, m), 9.12 (2H, s).

The carbapenem compounds according to the present invention may be formulated in various preparation forms.

FORMULATION EXAMPLE 1 (INJECTION):

(1) Injectable suspension:

| Compound (15) | 25.0 g |
|---|---|
| Methyl cellulose | 0.5 g |
| Polyvinyl pyrolidone | 0.05 g |
| Methyl p-oxybenzoate | 0.1 g |
| Polysolvate 80 | 0.1 g |
| Lidocaine hydrochloride | 0.5 g |
| Distilled water | to make 100 ml |

The above components were formulated to 100 ml of an injectable suspension.

(2) Lyophilization:

An appropriate amount of distilled water was added to 20 g of the sodium salt of the Compound (15) to make a total volume of 100 ml. The above solution (2.5 ml) was filled in vials so as for each vial to contain 500 mg of the sodium salt of Compound (15) and lyophilized. The lyophilized vial was mixed in situ with approximately 3-4 ml of distilled water to make an injectable solution.

(3) Powder:

The Compound (15) was filled in the amount of 250 mg in a vial and mixed in situ with about 3-4 ml of distilled water to make an injectable solution.

FORMULATION EXAMPLE 2

| Compound (15) | 250 mg |
|---|---|
| Lactose | 250 mg |
| Hydroxypropyl cellulose | 1 mg |
| Magnesium stearate | 10 mg |
| | 511 mg/tablet |

The above components were mixed with each other and punched into tablets in conventional manner. Such tablets, as required, may be formulated into sugar coatings or film coatings in conventional manner.

FORMULATION EXAMPLE 3 (TROCHE)

| Compound (15) | 200 mg |
|---|---|
| Sugar | 770 mg |
| Hydroxypropyl cellulose | 5 mg |
| Magnesium stearate | 20 mg |
| Flavor | 5 mg |
| | 1,000 mg/troche |

The component was mixed with each other and formulated into troches by punching in conventional manner.

FORMULATION EXAMPLE 4 (CAPSULES)

| Compound (15) | 500 mg |
|---|---|
| Magnesium stearate | 10 mg |
| | 510 mg/capsule |

The component was mixed with each other and filled in conventional hard gellatin capsules.

FORMULATION EXAMPLE 5 (DRY SYRUP)

| Compound (15) | 200 mg |
|---|---|
| Hydroxypropyl cellulose | 2 mg |
| Sugar | 793 mg |
| Flavor | 5 mg |
| | 1,000 mg |

The above components were mixed with each other and formulated into dry syrups in conventional manner.

FORMULATION EXAMPLE 6 (POWDERS)

| (1) Compound (15) | 200 mg |
|---|---|
| Lactose | 800 mg |
| | 1,000 mg |
| (2) Compound (15) | 250 mg |
| Lactose | 750 mg |
| | 1,000 mg |

Each of the components was mixed with each other and formulated in powders in conventional manner.

PREPARATION EXAMPLE 7 (SUPOSITORY)

| Compound (15) | 500 mg |
|---|---|
| Witepsol H-12 (Product of Dynamite Noble) | 700 mg |
| | 1,200 mg |

The above components were mixed with each other and formulated into supositories in conventional manner.

The (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate, including the various salt or charged acid forms, forms a crystalline structure in accordance with the following procedure. 45 mg (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate was dissolved in 4 ml water. The resultant solution was filtered using Membran ® filter (0.22 μm). The filtrate was lyophilized to give amorphous (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate. This amorphous form of (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate was then again dissolved in 0.4 ml water, and the resultant solution warmed to 40° C. to completely dissolve the (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate. After storage under refrigeration conditions for a period of 3 hours, the sample was inspected and crystals were observed. The crystalline (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate was washed with a small amount of 50% ethanolic solution in water, and the resultant crystals were dried at room temperature under a vacuum to yield 34 mg crystalline (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate (75.6%).

The crystalline form of (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate retains its potency over a prolonged period of time, whereas the amorphous form rapidly loses potency. For example, over a period of ten days, there is no appreciable loss of potency for the crystalline form, whereas the potency of the amorphous form is approximately 40% of the original value after a period of only ten days.

What is claimed is:

1. A method of treatment for controlling or preventing a bacterial infection in a subject which comprises administering to said subject an antibacterially effective amount of (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate or a pharmaceutically acceptable salt thereof.

2. An antibacterial composition comprising an antibacterially effective amount of (1R,5S,6S)-2-[(6,7-dihydro-5H-pyrazolo[1,2-a][1,2,4]triazolium-6-yl)]thio-6-[R-1-hydroxyethyl]-1-methyl-carbapenem-3-carboxylate or a pharmaceutically acceptable salt thereof, and a pharmaceutically acceptable carrier therefor.

* * * * *